United States Patent [19]
Castellano

[11] Patent Number: 6,156,008
[45] Date of Patent: Dec. 5, 2000

[54] DEVICE FOR AVOIDING SUBDERMAL HEMATOMAS FROM AN INJECTION

[76] Inventor: Thomas P. Castellano, 2730 Selby Ave., Los Angeles, Calif. 90064

[21] Appl. No.: 09/072,312

[22] Filed: May 4, 1998

[51] Int. Cl.[7] ............................... A61M 5/00; A61M 5/30
[52] U.S. Cl. .............................................. 604/116; 604/68
[58] Field of Search ................................ 604/68–72, 116, 604/115, 112, 131, 137, 140; 128/DIG. 1

[56] References Cited

U.S. PATENT DOCUMENTS

| 5,354,287 | 10/1994 | Wacks ..................................... 604/232 |
| 5,480,381 | 1/1996 | Weston ..................................... 604/68 |
| 5,730,723 | 3/1998 | Castellano et al. ........................ 604/68 |
| 5,851,198 | 12/1998 | Castellano et al. ........................ 604/68 |
| 5,993,412 | 11/1999 | Deily et al. ................................ 604/68 |

*Primary Examiner*—Sharon Kennedy
*Attorney, Agent, or Firm*—Pillsbury Madison & Sutro LLP

[57] ABSTRACT

An injection site detecting device is for detecting a suitable site for injecting liquid medication through a skin surface of a patient with an injector. The injection site locating device includes a sensor to detect and give an indication of a suitable injection site to minimize creation of subdermal hematomas from injection of the liquid medication by the injector. In particular, the sensor is a temperature sensor that detects the presence of high and/or low blood flows and indicates that a suitable injection site is over the low blood flow. The sensor indicates a suitable injection site by changing color due to changes in temperature or by providing a sound signal due to changes in temperature. Generally, low blood flows representing suitable injection sites are detected by a stable temperature in the range of 92.0 to 95.5° Fahrenheit, and high blood flows representing an unsuitable injection site are detected by a stable temperature in the range of 95.6 to 99.0° Fahrenheit.

10 Claims, 4 Drawing Sheets

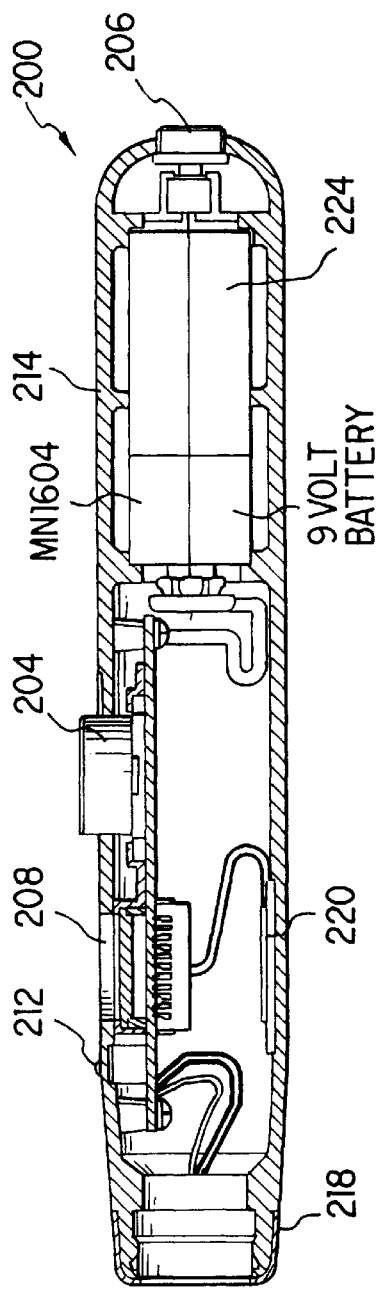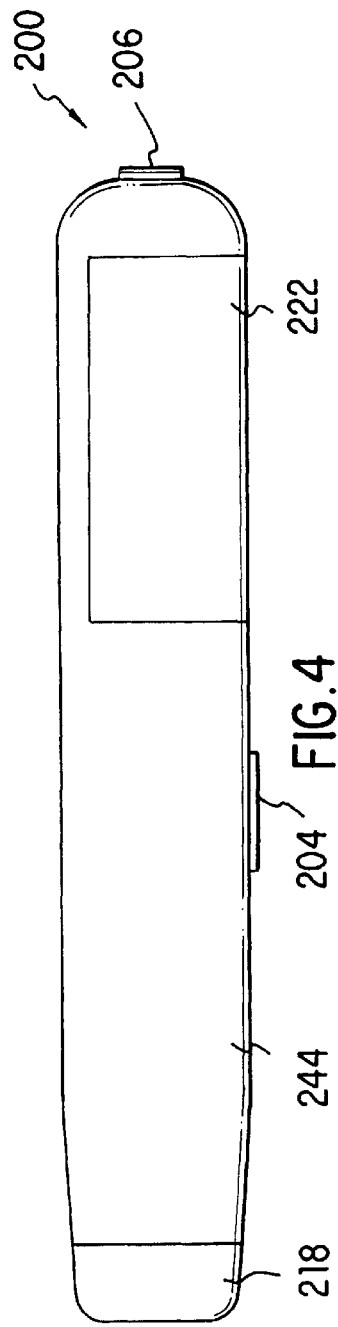

DEVICE FOR AVOIDING SUBDERMAL HEMATOMAS FROM AN INJECTION

FIELD OF THE INVENTION

This invention relates to devices and methods for avoiding subdermal hematomas during an injection, and in particular, embodiments for avoiding subdermal hematomas from the use of a needle-less injector or syringe, and in a needle-less injector with a built-in capability to minimize the occurrence of subdermal hematomas from needle-less injections.

BACKGROUND OF THE INVENTION

Typically, injections are performed with syringes that pierce the skin with a needle to deliver medication to a desired location on a body. Piercing the skin in an area including or over high blood flows (otherwise know as free blood flows), such as from the presence of vascular bundles, arteries and/or veins, can cause the formation of subdermal hematomas (or bruising). These subdermal hematomas are unsightly, taking several weeks to heal, and are generally painful. If the needles are dull or have burrs, left over from manufacturing, this compounds the problem of creating subdermal hematomas.

As an alterative to needle delivery injections, needle-less medication injections have been performed with "permanent gun" instruments, generally referred to as "jet injectors". These devices use either a compression spring or a compressed inert gas to propel the fluid medication (via a push rod plunger) through a small orifice (an injector nozzle) which rests perpendicular to and against the injection site. The fluid medication is generally accelerated at a high rate to a speed of between about 800 feet per second (fps) and 1,200 fps (approximately 244 and 366 meters per second, respectively). This causes the fluid to pierce through the skin surface without the use of a needle, resulting in the medication being deposited in a flower pattern under the skin surface. This method of medication delivery is referred to as a subcutaneous injection. Again, piercing the skin in an area including or over high blood flows (such as from vascular bundles, arteries and veins) can cause the formation of subdermal hematomas (or bruising). Also with jet injectors, a used and worn delivery orifice can slow down the delivery speed of the injected fluid, which results in inadequate penetration and causes further subdermal hematomas (or bruising) of the skin at the injection site.

A drawback to all of these devices is that there is no way to determine if subdermal hematomas (or bruising) are likely to occur prior to administering an injection.

SUMMARY OF THE DISCLOSURE

It is an object of an embodiment of the present invention to provide an improved device and method for avoiding subdermal hematomas with syringes, needle-less injectors, or the like, that obviates for practical purposes, the above-mentioned limitations.

According to an embodiment of the present invention, an injection site detecting device is for detecting a suitable site for injecting liquid medication through a skin surface of a patient with an injector. The injection site locating device includes a sensor to detect and give an indication of a suitable injection site to minimize creation of subdermal hematomas from injection of the liquid medication by the injector. In particular embodiments, the sensor is a temperature sensor that detects the presence of high and/or low blood flows and indicates that a suitable injection site is over the low blood flow. The sensor indicates a suitable injection site by changing color due to changes in temperature or by providing a sound signal due to changes in temperature. In preferred embodiments, low blood flows representing suitable injection sites are detected by a stable temperature in the range of 92.0 to 95.5° Fahrenheit, and high blood flows representing an unsuitable injection site are detected by a stable temperature in the range of 95.6 to 99.0° Fahrenheit. The preferred sensor utilizes infrared radiation to detect the suitable injection site.

In alternative embodiments, the sensor utilizes changes in electrical resistance of the skin of the patient to detect the suitable injection site. In other alternative embodiments, the sensor utilizes ultrasound to detect the suitable injection site. In yet other alternative embodiments, the sensor utilizes optical measurements to detect the suitable injection site.

In accordance with further embodiments of the present invention, a needle-less injector suitable for injecting liquid medication through a skin surface of a patient includes a needle-less injection mechanisms and a sensor. The needle-less injection mechanism is for injecting the liquid medication. The sensor is coupled to the needle-less injection mechanism to detect and give an indication of a suitable injection site to minimize creation of subdermal hematomas from injection of the liquid medication by the needle-less injection mechanism. In preferred embodiments, the sensor is a temperature sensor that detects the presence of high and low blood flows and indicates that a suitable injection site is over the low blood flow, and the sensor indicates a suitable injection site by changing color.

According to further embodiments of the needle-less injector mechanism includes a housing, a driver and a trigger. The housing contains the liquid medication to be injected into the patient. The driver forces the medication out of the housing at a sufficient speed to pierce the skin surface of the patient. The resistance sensitive trigger is coupled to the driver and is used to activate the driver to force the liquid medication out of the housing. The resistance sensitive trigger is activated upon application of a predetermined amount of pressure to the resistance sensitive trigger that is opposed by a predetermined amount of resistance from the skin surface of the patient. The predetermined amount of resistance results from the housing having contact with the skin surface of the patient, and when this predetermined amount of resistance is reached the liquid medication is forced out of the housing by the driver to pierce the skin surface of the patient.

In further embodiments, the housing of the needle-less injector includes a face that is adapted to align the housing to produce the predetermined amount of resistance to allow for activation of the resistance sensitive trigger. Also, the resistance sensitive trigger is preferably coupled to the housing to permit axial movement of the resistance sensitive trigger along the housing. However, the fit tolerances between the housing and the resistance sensitive trigger are selected to permit activation of the resistance sensitive trigger when the housing is aligned between 0 and 10 degrees off an axis perpendicular to the skin surface of the patient. In addition, the resistance sensitive trigger is preferably positioned to be between the skin surface of the patient and an activating appendage (such as a hand, arm or the like) of a user when activating the driver to force the medication out from the housing.

Other features and advantages of the invention will become apparent from the following detailed description, taken in conjunction with the accompanying drawings which illustrate, by way of example, various features of embodiments of the invention.

BRIEF DESCRIPTION OF THE DRAWINGS

A detailed description of embodiments of the invention will be made with reference to the accompanying drawings, wherein like numerals designate corresponding parts in the several figures.

FIG. 3 is a cross-sectional view of the injection site detector as shown along the line 3—3 in FIG. 2.

FIG. 4 is a side view of the injection site detector shown in FIG. 2.

DETAILED DESCRIPTION OF THE PREFERRED EMBODIMENTS

Figure 1:
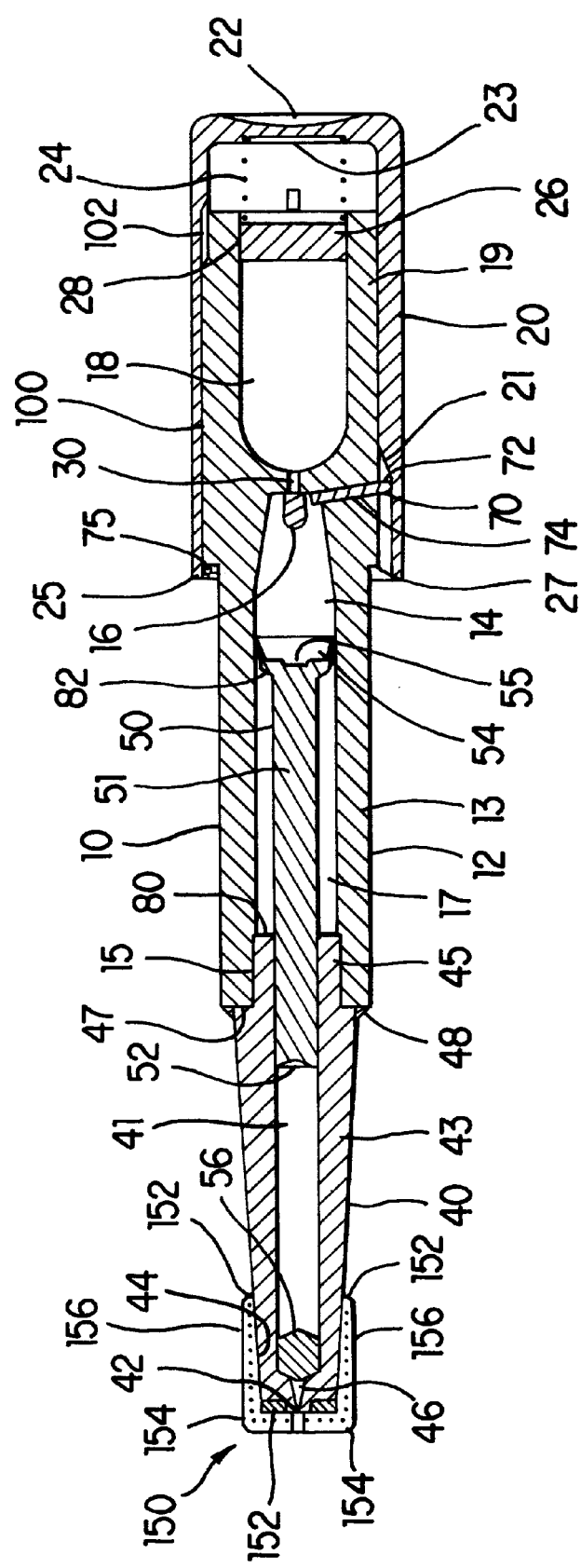
FIG. 1 is a cross-sectional diagram of a needle-less injector device according to an embodiment of the invention.

As shown in the drawings for purposes of illustration, the invention is embodied in a device and method for avoiding or minimizing subdermal hematomas (or bruises) from an injection. In preferred embodiments of the present invention, the device and methods are for avoiding or minimizing subdermal hematomas (bruising) from a needle-less injection. Preferably, the device is used in conjunction with, or are attached to, a single use disposable needle-less injector, such as that disclosed in U.S. Pat. No. 5,730,723 issued Mar. 24, 1998 and U.S. Pat. No. 5,851,198, issued Dec. 22, 1998 which are here incorporated by reference. However, it will be recognized that further embodiments of the invention may be used to prevent subdermal hematomas in multiple use needle-less injectors, conventional syringes, infusion injections and the like. In further embodiments, the device may be used to locate veins and arteries for IV drips or the like.

In one embodiment of the present invention, a single-use needle-less injector device 10 includes a sensor 150 that utilizes temperature to locate an area under the skin that is generally free of high blood flow (i.e., areas free of vascular bundles, arteries and/or veins). For instance, the normal skin temperatures average between 92.0° to about 95.5° F., while skin that is directly over flowing blood (e.g., vascular bundles, arteries and veins) has an average temperature between 95.6° F. and 99.0° F. For example, high blood flows are often found at 3 mm or deeper under the skin. Typical jet injectors or syringes deliver medications at of depth of between 3–8 mm deep, with the depth being dependent on the medication and the type of tissue being injected into. To minimize the formation of subdermal hematomas (or bruising), it is best to avoid vascular bundles, arteries, veins and even large capillaries, if possible. The smaller the blood flow in the area of the injection site, the lower the likelihood that subdermal hematomas will result from the injection.

With a sensor 150 that is heat sensitive, a change to a green color indicates that the face of an ampule, that is pressed against the skin, is properly positioned for an injection to avoid or minimize the creation of subdermal hematomas (bruising). Preferably, in operation, the user positions the sensor 150 and face (and orifice) 42 of the ampule (or liquid chamber) 41 against a desired injection site and waits 10 seconds to allow the sensor to reach thermal equilibrium. Generally, in about 10 seconds, if the sensor 150 detects a stable temperature between 92.0 and 95.5° F., the sensor 150 turns green indicating an acceptable site, the user can then administer the injection. If the sensor 150 remains red (meaning a temperature that is too high or too low), the user moves the location of the injector 10 to a site in which the sensor 150 gives a green color. In alterative embodiments, different times ranging from 5 seconds to 60 seconds may be used, with the time being dependent on the sensitivity of the sensor 150, and the temperature of the ampule 41 holding the medication in the injector 10. In further embodiments, different colors may be used to indicate an acceptable or unacceptable injection site.

In still further embodiments, the injectors 10 are stored in a heating tray (not shown) that heats the sensor 150 to a temperature above 99° Fahrenheit, so that the injector will not feel uncomfortable (or cold) against the injection site, and the sensor 150 will detect a drop in temperature when an acceptable injection site is found. This approach has the advantage that a user does not give an injection before the sensor has been given sufficient time to reach thermal equilibrium with the higher temperature over high blood flows (e.g., vascular bundles, arteries and veins). The sensor 150 starts out at a high temperature and the proper injection site cools the sensor 150 to provide a positive indication, while high blood flows prevent reduction in the temperature of the sensor that would indicate an acceptable injection site.

In preferred embodiments, the sensor 150 has an insulating layer 152 that minimizes the sensor 150 sensitivity to the temperature of the ampule 41 of the needle-less injector 10. Thus, a medication that needs to be refrigerated will not prevent the sensor 150 from detecting the temperature of the skin or require the ampule 41 to reach a stable temperature near the temperature of the skin.

The operation of the needle-less injector 10 device according to the preferred embodiment will now be discussed. Initially at the manufacturing facility, the injection device 10 is pre-filled with medication in the liquid chamber 41 and is pre-filled with compressed gas in the first gas chamber 18. During manufacture, a sensor 150 is normally attached with an opening over the orifice 42. Alternatively, the user may place the sensor 150 on the injector 10 prior to use. The user (or an operator) unscrews (or unsnaps) the cap 60 from the main body 12, thus revealing the orifice 42 of the injector device 10. The user then positions the injector device 10 perpendicularly against the skin surface to provide firm and secure contact of the orifice 42 against the skin surface. The user then waits for a predetermined period of time to determine if an acceptable injection site has been located. If an acceptable site is found, the injection proceeds, or if an unacceptable site is found, the injector 10 is moved until an acceptable injection site is detected.

The injector device 10 requires the device 10 to be properly oriented and in contact with the skin of the patient, since the injector device 10 is designed so that it cannot be activated or discharged without the device 10 being placed against the skin surface. Otherwise, with a fluid delivery speed of about 800 fps or higher, a jet injector could injure a person's eye or other part of the body. In addition, if the jet injector were not positioned properly against the injection site, and the injection device were activated, the dosage can be short of the measured dosage, thereby creating wetting on the skin surface, which leads to additional problems associated with improper dosage amounts.

As the trigger portion 22 of the actuating member 20 is depressed, the skin surface of the patient resists the pressure being applied to the actuating member 20 of the resistance sensitive trigger and the coil spring 24 is compressed between the chamber plug 26 and the spring surface 23. Sufficient pressure (generally a minimum of 2.2 lbs/in$^2$ (1.0 kg/2.5 cm$^2$)) must be applied at the trigger portion 22 to overcome the tension of the coil spring 24. Concurrently, as the inclined region 21 pushes against the lever 70, the lever 70 is pushed inward toward the center axis of the main body 12. As the actuating member 20 is pressed further against the skin surface, the lever 70 pushes against the side of the release tab 16, tearing (or breaking off) the release tab 16. This exposes the opening of the passageway 30, and the compressed gas stored in the first gas chamber 18 is released into second gas chamber 14. When sufficient pressure is built up inside the second gas chamber 14, the piston 50 is pushed forward so that it slides forward in the liquid chamber 41. The seal around the head 54 of the piston 50 substantially prevents any gas from leaking into the other parts of the elongated cavity. The forward movement of the piston 50 causes the front surface 52 of the piston 50 to make contact with the rear surface of the plunger 56, to move the plunger 56 forward. As the plunger 56 moves forward, the liquid medication exits from the orifice 42 at a high speed and penetrates the skin surface at the injection site.

In preferred embodiments, the temperature sensor 150 is a strip of temperature sensitive material 154, that undergoes a change of color as it reaches different temperatures. The strip 154 is attached as a patch at the end of the needle-less injector 10 on the face (or orifice) 42 of the ampule 41 with a small hole over the orifice 42 to permit the medication to be delivered into the skin unimpeded by the temperature sensor. In particular embodiments, the temperature sensor 150 also has extensions 156 that wrap around the sides of the ampule 41 so that the color change can be more readily observed without removing the needle-less injector 10 from the injection site. After a period of time (typically, 5–20 seconds), the temperature sensor will change to green if there is no high blood flow through vascular bundles, veins and arteries in the area of the injection. The injection can then proceed in a normal manner, with a minimized risk of creating subdermal hematomas. In alternative embodiments, a temperature sensor strip 154 may be omitted and the ampule of the needle-less injector 10 may be formed from a color change-temperature sensitive plastic, which turns green, when positioned over a proper injection site. In further embodiments, the temperature sensitive material may change to a different color to indicate an improper site (such as red).

In another alternative embodiment, temperature sensitive strips or patches (not shown) may be placed on the skin to indicate acceptable injections sites. The patch or strip is then removed just before an injection is administered.

Figure 2:
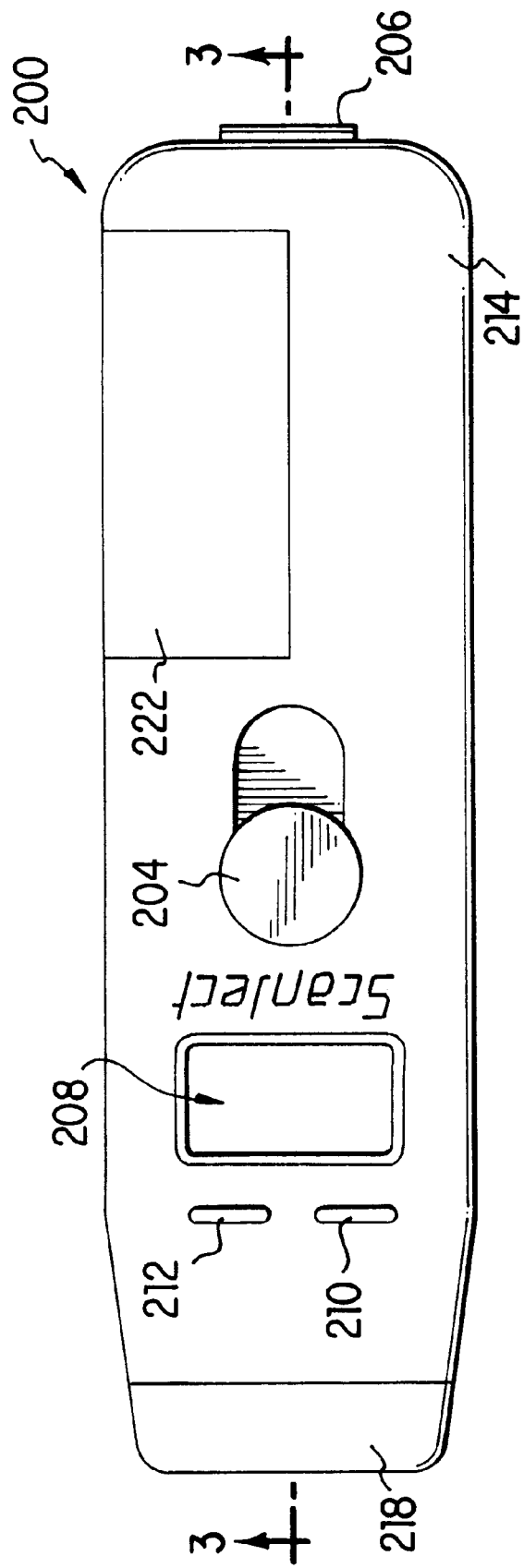
FIG. 2 is a top plan view of an injection site detector in accordance with an embodiment of the present invention.
Figure 6:
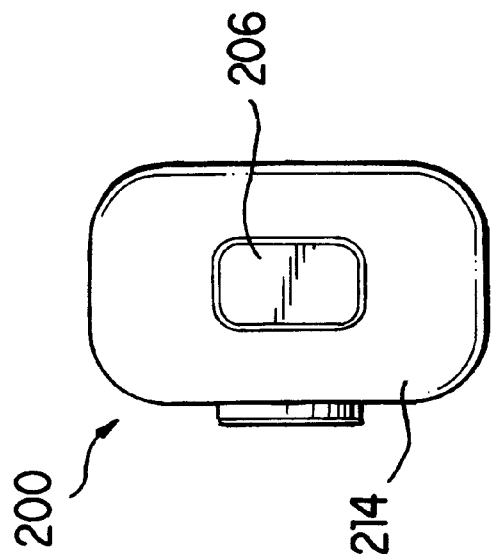
FIG. 6 is an end view of the activation end of the injection site detector shown in FIG. 2.
Figure 5:
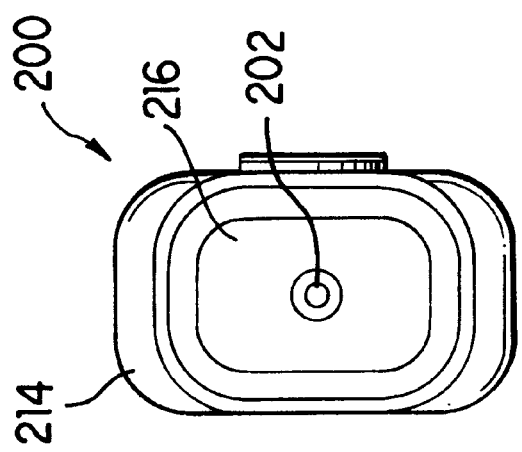
FIG. 5 is an end view of the sensor end of the injection site detector shown in FIG. 2.

As shown in FIGS. 2–6, a separate injection site detecting device 200 in accordance with an embodiment of the present invention may be used with syringes or needle-less injectors. The injection site detecting device 200 is ideally suited for use in hospitals, clinic, vaccination centers and by chronic users of injection devices.

The injection site detecting device 200 includes an infrared temperature sensor 202, a first activation button 204, a second activation button 206, an LCD (liquid crystal display) 208, an acceptable site LED 210, and an unacceptable site LED 212 held in a housing 214.

The infrared temperature senor 202 is provided in a recessed opaque tunnel 216 to minimize reflections from external sources and to position the sensor 202 at the desired distance from the skin surface to obtain accurate readings. In preferred embodiments, the opening of the tunnel 216 is covered with an infrared transparent, replaceable and disposable membrane 218 that is replaced after each use to minimize contamination between different patients. The use of a separate injection site detecting device 200 allows for the construction of a more complicated device that permits the use of more sophisticated techniques and allows for re-use of the device. For example, the infrared temperature sensor 202 is used to measure the attenuation of an infrared signal transmitted into the skin, and which varies as a function of temperature or blood flow, which is generally quicker and more accurate than a color changing temperature sensitive material. The resulting attenuation of the infrared signal is converted into a temperature and an indication of the acceptability of the injection site.

The housing 214 holds the two activation buttons 204 and 206. Preferably, each operates the injection site detecting device 200 in the same manner. Generally, the activation button 204 is better positioned for use by a doctor or medical technician, while the second activation button 206 is better positioned for self detection by the patient. The LCD 208 in the housing 214 is used to provide visual prompts and instructions to the user, as they detect a suitable injection site (such as "Wait", "Processing", "Error" or the like).

The acceptable site LED 210 illuminates with a green color when an acceptable site, that falls within the parameters held by the device, is detected. If a test is in progress, the unacceptable site LED 212 will generally blink to indicate, along with an indication on the LCD 208, that the device 200 is still monitoring the temperature. If the final results are negative, and the site is unacceptable, the unacceptable LED 212 will remain a steady red. In alternative embodiments, the LEDS 210 and 212 may be omitted, and the acceptability may only be indicated on the LCD 208. In particular embodiments, the injection site detecting device 200 includes a piezoelectric buzzer 220 (see FIG. 3) that provides an audible indication of the acceptability or unacceptability of the proposed injection site.

In preferred embodiments, the housing 214 includes a battery compartment 222 that holds a 9 volt battery 224 to provide the power for the injection site detecting device 200. In alternative embodiments, the injection site detecting device 200 may include a DC power port (not shown) that can be connected to a power adapter, solar cells, or the like.

In operation, the user places a thin membrane 218 over the opening in the opaque tunnel 216 on the injection site detecting device 200. Next the user places the thin membrane against the surface of the skin, where the user intend to administer an injection, to position the sensor 202 for proper determination of the acceptability of the proposed injection site. Either one of the activation buttons 204 and 206 are activated, and the test proceeds automatically. The LCD 208 will inform the user of the status of the test as it proceeds. Upon completion of the test, the piezoelectric buzzer 220 will sound, and one of the LEDs 210 and 212 will remain lighted. If the acceptable (green) LED 210 is lighted, the user removes the injection site detecting device 200 and positions the injector device on the injection site and administers and injection. If the unacceptable (red) LED is lighted, the user moves the injection site detecting device 200 to a new location and repeats the process until an acceptable injection site is detected.

In alternative embodiments, different sensor techniques may be utilized instead of the infrared temperature readings.

For instance, optical measurements of the absorbance of light may be used to indicate the presence of vascular bundles, arteries and/or veins. In addition, ultrasound registration and electrical resistance changes in the skin may be used. In further embodiments, the injection site detecting device 200 may include a marking capability (not shown), that uses a pen, stylus or needle with an ink or dye (either temporary or permanent) to indicate an acceptable injection site for easier recall at a later time, or the like. This is particularly useful for users that must have repeated injections, such as diabetics or for persons taking regular allergy injections or the like. It is also useful in vaccination clinics, where one technician may find the suitable injection sites, and another administers the injections.

In preferred embodiments, the injection site detecting device 200 is a small, portable, pen-sized device that is used separately from an injection device. However, in alternative embodiments, the injection site detecting device 200 may be incorporated as part of multiple injection devices, such as reusable jet injectors or multi-use injectors with replaceable needles, In still further embodiments, the injection site detecting device 200 may be used to indicate and find areas of high blood flows, such as from arteries and veins, to facilitate administration and insertion of IV drips and the like.

While the description above refers to particular embodiments of the present invention, it will be understood that many modifications may be made without departing from the spirit thereof. The accompanying claims are intended to cover such modifications as would fall within the true scope and spirit of the present invention.

The presently disclosed embodiments are therefore to be considered in all respects as illustrative and not restrictive, the scope of the invention being indicated by the appended claims, rather than the foregoing description, and all changes which come within the meaning and range of equivalency of the claims are therefore intended to be embraced therein.

What is claimed is:

1. A needle-less injector suitable for injecting liquid medication through a skin surface of a patient, the needle-less injector comprising:
    a needle-less injection mechanism for injecting the liquid medication; and
    a sensor coupled to the needle-less injection mechanism to detect and give an indication of a suitable injection site to minimize creation of subdermal hematomas from injection of the liquid medication by the needle-less injection mechanism.

2. The needle-less injector in accordance with claim 1, wherein the sensor is a temperature sensor that detects the presence of high and low blood flows and indicates that a suitable injection site is over the low blood flow.

3. The needle-less injector in accordance with claim 2, wherein the sensor indicates a suitable injection site by changing color.

4. The needle-less injector in accordance with claim 2, wherein the needle-less injection mechanism includes:
    a housing containing the liquid medication;
    a driver that forces the medication out of the housing at a sufficient speed to pierce the skin surface of the patient;
    a resistance sensitive trigger coupled to the driver and which activates the driver to force the liquid medication out of the housing upon application of a predetermined amount of pressure to the resistance sensitive trigger that is opposed by a predetermined amount of resistance from the skin surface of the patient resulting from the housing having contact with the skin surface of the patient such that the forced out liquid medication will pierce the skin surface of the patient.

5. The needle-less injector in accordance with claim 4, further including a face on the housing adapted to align the housing to produce the predetermined amount of resistance to allow for activation of the resistance sensitive trigger.

6. The needle-less injector in accordance with claim 4, wherein the resistance sensitive trigger is coupled to the housing to permit axial movement of the resistance sensitive trigger along the housing, wherein fit tolerances between the housing and the resistance sensitive trigger permit activation of the resistance sensitive trigger when the housing is aligned between 0 and 15 degrees off an axis perpendicular to the skin surface of the patient.

7. The needle-less injector in accordance with claim 4, wherein the resistance sensitive trigger is positioned to be between the skin surface of the patient and an activating appendage of a user when activating the driver to force the medication out from the housing.

8. The needle-less injector in accordance with claim 4, wherein the resistance sensitive trigger includes a resistance element that activates at a lower amount of pressure than the predetermined amount of resistance by the skin surface of the patient.

9. The needle-less injector in accordance with claim 8, wherein the resistance sensitive trigger includes a cap slidably attached to the housing and wherein the resistance element includes a spring coupled between the housing and the cap, wherein upon application of the predetermined amount of pressure to the cap of the resistance sensitive trigger the spring compresses, when the opposing resistance from the skin surface of the patient reaches the predetermined amount of resistance, to activate the driver to force the liquid medication out of the housing to pierce the skin surface of the patient.

10. The needle-less injector in accordance with claim 4, wherein the needle-less injector is compressed gas activated.

* * * * *